(12) United States Patent
Malamud (10) Patent No.: US 7,236,560 B2
(45) Date of Patent: Jun. 26, 2007

(54) ANTI-SCATTERING X-RAY SHIELDING FOR CT SCANNERS

(75) Inventor: Gabriel Malamud, Benyamina (IL)

(73) Assignee: Koninklijke Philips Electronics N.V., Eindhoven (NL)

( * ) Notice: Subject to any disclaimer, the term of this patent is extended or adjusted under 35 U.S.C. 154(b) by 97 days.

(21) Appl. No.: 10/526,736

(22) PCT Filed: Sep. 4, 2002

(86) PCT No.: PCT/IL02/00729

§ 371 (c)(1),
(2), (4) Date: Jul. 21, 2005

(87) PCT Pub. No.: WO2004/023123

PCT Pub. Date: Mar. 18, 2004

(65) Prior Publication Data

US 2006/0039527 A1  Feb. 23, 2006

(51) Int. Cl.
*G01N 23/00* (2006.01)
(52) U.S. Cl. .................. 378/7; 378/154; 250/505.1
(58) Field of Classification Search ............... 378/154, 378/147, 149, 7; 250/505.1
See application file for complete search history.

(56) References Cited

U.S. PATENT DOCUMENTS

| 5,099,134 | A | 3/1992 | Hase et al. |
| 5,949,850 | A | 9/1999 | Tang |
| 6,134,301 | A | 10/2000 | Mruzek et al. |
| 6,175,615 | B1 | 1/2001 | Guru et al. |
| 6,370,227 | B1 | 4/2002 | Guru et al. |
| 6,377,661 | B1 | 4/2002 | Guru et al. |
| 6,784,432 | B2 * | 8/2004 | Wieczorek ............ 250/367 |
| 6,895,080 | B2 * | 5/2005 | Baba et al. ............ 378/154 |

FOREIGN PATENT DOCUMENTS

| EP | 1 045 398 A2 | 10/2000 |
| JP | 2000093418 | 4/2000 |
| JP | 2001046364 | 2/2001 |
| WO | WO 02/04932 A1 | 1/2002 |

* cited by examiner

*Primary Examiner*—Jurie Yun
(74) *Attorney, Agent, or Firm*—Thomas M. Lundin (57) ABSTRACT

A CT scanner comprising a stator and a rotor having an axis of rotation mounted to the stator so that the rotor is rotatable about the axis of rotation comprising: an X-ray source mounted to the rotor, said X-ray source having a focal spot from which X-rays emanate; an X-ray detector array comprising a matrix of rows and columns of X-ray detectors; anti-scattering (AS) material for absorbing X-rays positioned between columns of the X-ray detectors; and anti-scattering (AS) material for absorbing X-rays positioned between rows of the X-ray detectors, whereby the AS material is located between every other row and/or column of detectors, respectively. Furthermore, the thickness and/or height of the foils between rows may be different from the thickness and/or height of the foils between columns.

10 Claims, 9 Drawing Sheets

ANTI-SCATTERING X-RAY SHIELDING FOR CT SCANNERS

FIELD OF THE INVENTION

The present invention relates to computerized tomography (CT) X-ray imaging and in particular to methods for shielding X-ray detectors in a CT imaging system from scattered X-rays.

BACKGROUND OF THE INVENTION

In CT X-ray imaging of a patient, X-rays are used to image internal structure and features of a region of the person's body. The imaging is performed by a CT-imaging system, hereinafter referred to as a "CT scanner" that images internal structure and features of a plurality of contiguous, relatively thin planar slices of the body region using X-rays.

The CT scanner generally comprises an X-ray source that provides a planar, fan-shaped X-ray beam emanating from a focal spot of the X-ray source and an array of closely spaced X-ray detectors that are substantially coplanar with the fan-beam and face the X-ray source. The X-ray source and array of detectors are mounted in a gantry so that a person being imaged with the CT scanner, generally lying on an appropriate support couch, can be positioned within the gantry between the X-ray source and the array of detectors. The gantry and couch are moveable relative to each other so that the X-ray source and detector array can be positioned axially, along a "z-axis", at desired locations along the patient's body.

The gantry comprises a stationary structure, referred to as a stator, and a rotary element, referred to as a rotor, which is mounted to the stator so that the rotor is rotatable about the z-axis. In third generation CT scanners the X-ray source and detectors are mounted to the rotor. The detectors are generally arrayed along an arc of a circle having its plane perpendicular to the z-axis and its center located at a focal spot of the scanner's X-ray source. Hereinafter, such an array of detectors along an arc of a circle is referred to as a "row" of detectors. Angular position of the rotor about the z-axis is controllable so that the X-ray source can be positioned at desired angles, referred to as "view angles", around the patient's body. In fourth generation CT scanners the X-ray detector array comprises detectors positioned around the perimeter of a circle to form a full circle of detectors. The circle of detectors is stationary and the X-ray source is mounted to the rotor and rotates with the rotor.

To image a slice in a region of a patient's body, the X-ray source is positioned at the z-axis coordinate of the slice and rotated around the slice through an angle of at least 180° to illuminate the slice with X-rays from a plurality of different view angles. At each view angle, detectors in the array of detectors measure intensity of X-rays from the source that pass through the slice. The intensity of X-rays measured by a particular detector in the array of detectors is a function of an amount by which X-rays are attenuated by material in the slice along a straight-line path length from the X-ray source, through the particular slice, to the detector.

The measurements provided by the X-ray detectors are processed using algorithms known in the art to provide a map of the absorption coefficient of the material in the slice as a function of position. Maps of the absorption coefficient for the plurality of contiguous slices in the region of the patient's body are used to display and identify internal organs and features of the region.

Many older CT scanners are single slice scanners that comprise only a single row (i.e. also a single circle for fourth generation CT scanners) of X-ray detectors and image only one slice of a region of a person's body at a time. Most modern CT scanners are multislice CT scanners designed to simultaneously image a plurality of slices of a patient. A multislice CT scanner comprises a plurality of parallel rows (or circles for fourth generation scanners) of X-ray detectors closely spaced one next to the other along the z-axis. The detector array of a multislice CT scanner is thus a "two-dimensional" (ignoring the curvature of the rows) matrix of rows and columns of detectors. A column of detectors in the array refers to detectors comprised in the rows of detectors that lie along a same line parallel to the z-axis of the scanner.

A multislice scanner can be operated to simultaneously image a number of slices of a patient up to a maximum number of slices equal to the number of rows of detectors. Typically, signals from detectors in a multislice scanner are combined in accordance with any of various algorithms known in the art to simultaneously image a plurality of slices that is less than the number of rows of detectors. A present day conventional multislice scanner may image as many as four to sixteen slices of a region of a patient simultaneously and scanners that simultaneously image more than sixteen slices are under development.

Ideally, each detector in a CT scanner measures intensity of X-rays that reach the detector after passage along a substantially straight-line path from the X-ray source to the detector. Therefore, ideally, only those X-rays that are neither absorbed by the material along the path from the X-ray source to the detector nor scattered by the material at angles that prevent the X-rays from being incident on the detector reach the detector. However, X-rays that are scattered out of the path from the X-ray source to one X-ray detector in the detector array of the CT scanner are generally scattered in directions towards other X-ray detectors in the scanner detector array. If these scattered X-rays are incident on the other X-ray detectors, they can generate error in measurements provided by the other detectors and degrade quality of an image provided by the CT scanner.

To reduce "scattering errors" in a CT scanner, X-ray detectors in the scanner's detector array are generally shielded from scattered X-rays. "Anti-scattering" shielding, hereinafter "AS shielding", for a detector array of a multi-slice CT scanner usually comprises a thin planar baffle foil, hereinafter an "AS foil", formed from a suitable X-ray absorbing material positioned between each column of detectors in the array. The plane of each AS foil is parallel to the z-axis and oriented so that it intersects the focal spot of the X-ray source, or a centroid of the focal spot if a deflecting focal spot is used. Hereinafter, a focal spot of an X-ray source is understood to mean a focal spot or, for a CT scanner having a deflecting focal spot, the centroid of the focal spot. For single slice CT scanners the AS foils are relatively effective in moderating effects of scattered X-rays on detector accuracy and image quality. However, the X-ray fan-beam in a multislice scanner is substantially thicker along the z-axis than the X-ray fan-beam in single slice scanners. As a result, detectors in a multislice CT scanner are potentially exposed to substantially more sources of scattered X-rays and thereby to a greater flux of scattered X-rays than are detectors in a single slice CT scanner.

To cope with increased flux of scattered X-rays in a multislice CT scanner, AS foils in a multislice scanner are often made higher than AS foils in a typical single slice scanner. However, a height to which AS foils can be fabricated is limited by production tolerances. As the height of AS foils is increased, the foils have to be fabricated and positioned to ever-finer tolerances. For example, as the height of AS foils in a CT scanner increases, the AS foils have to be aligned with the focal spot of the scanner's X-ray source to a greater degree of accuracy. To an extent that an AS foil is misaligned with the focal spot or its surface is compromised by inhomogeneities, it may shadow to a greater extent X-ray detectors adjacent to the AS foil. Shadowing alters the detection efficiency of a shadowed X-ray detector and may generate artifacts in images generated by the multislice CT scanner. In addition, shadowing, when it exists, is often unstable and may change from time to time. As a result, it can be difficult to compensate images provided by the CT scanner for artifacts introduced by shadowing.

It is noted that because of the geometry of fourth generation CT scanners, it is generally not possible to provide anti-scattering shielding for detectors comprised in a fourth generation CT scanner that does not result in undesirable shadowing of the detectors. As a result anti-scattering shielding is usually not provided for fourth generation scanners.

For multislice scanners, as the number of slices simultaneously imaged increases, the problem of scattering error is exacerbated As it does not seem possible to deal with the problem simply by increasing the height of AS foils used to shield the detectors, new solutions to scattering error are required.

SUMMARY OF THE INVENTION

An aspect of some embodiments of the present invention relates to providing an improved system for shielding X-ray detectors in a detector array of a multislice CT scanner from scattered X-rays.

An aspect of some embodiments of the present invention relates to providing AS shielding for X-ray detectors in a detector array of a multislice CT scanner comprising AS foils along at least two different directions.

A direction of an AS foil of a CT scanner is defined as a direction of a line of intersection of the plane of the AS foil with the surface of the X-ray detector array. For convenience, features and elements on the surface of the detector array are located using two coordinates, a z-coordinate measured along the z-axis and an "s" coordinate measured along a line, an "s-axis", in the surface of the detector array parallel to the rows of detectors in the array. Direction of an AS foil, i.e. the direction of its line of intersection with the X-ray detector array, is determined with reference to the z and s axes. Prior art AS foils described above, which are parallel to the columns of detectors in a CT scanner detector array, are therefore "z-axis" AS foils.

In an embodiment of the present invention, AS shielding comprises s-axis AS foils parallel to the rows of the detectors in the multislice scanner's detector array as well as z-axis column AS foils. For a given maximum AS foil height, the added s-axis AS foils provide efficient added shielding against scattered X-rays resulting from the relatively large dimension, thickness, of the fan-beam of the multislice scanner along the z-axis.

According to an aspect of some embodiments of the present invention, for each X-ray detector, from a perspective of an origin of a coordinate system located at the center of the X-ray detector, the AS shielding configuration is similar.

Configuration similarity of the AS shielding reduces possible artifacts in an image provided by the multislice scanner that might result from differences in the energy spectrum of X-rays reaching different detectors caused by differences in the AS shielding protecting the different detectors. In accordance with some embodiments of the present invention, to within a parity transformation and/or a rotation transformation, the AS shielding of any two X-ray detectors of the same size and shape, as seen from their respective coordinate systems, are substantially identical.

There is therefore provided, in accordance with an embodiment of the present invention, a CT scanner comprising a stator and a rotor having an axis of rotation mounted to the stator so that the rotor is rotatable about the axis of rotation comprising: an X-ray source mounted to the rotor, said X-ray source having a focal spot from which X-rays emanate; an X-ray detector array comprising a matrix of rows and columns of X-ray detectors; anti-scattering (AS) material for absorbing X-rays positioned between columns of the X-ray detectors; and anti-scattering (AS) material for absorbing X-rays positioned between rows of the X-ray detectors.

Optionally, as seen from a perspective of a first coordinate system located in substantially any first detector of the detector array and a homologous coordinate system located in substantially any second detector of the detector array, the AS material has substantially a same configuration to within a parity transformation and/or a rotation transformation Optionally, the AS material is located between every other row of detectors. Additionally or alternatively, the AS material is located between every other column of detectors.

In some embodiments of the present invention the AS material is formed in a shape of a thin foil for which for any point on the foil a segment of a line from the focal point of the X-ray source to the point lies substantially within or on the surface of the foil.

Optionally, foil between columns of detectors extends towards the focal point to a height relative to the detector array that is different from a height to which foil located between columns of detectors extends towards the focal point. Additionally or alternatively, thickness of the foil between rows is different from thickness of the foil between column.

In some embodiments of the present invention, the detectors have a hexagonal shape and the foil is shaped to follow the hexagonal shape of the detectors.

BRIEF DESCRIPTION OF FIGURES

Non-limiting examples of embodiments of the present invention are described below with reference to figures attached hereto and listed below. In the figures, identical structures, elements or parts that appear in more than one figure are generally labeled with a same numeral in all the figures in which they appear. Dimensions of components and features shown in the figures are chosen for convenience and clarity of presentation and are not necessarily shown to scale.

DESCRIPTION OF EXEMPLARY EMBODIMENTS

Figure 1A:
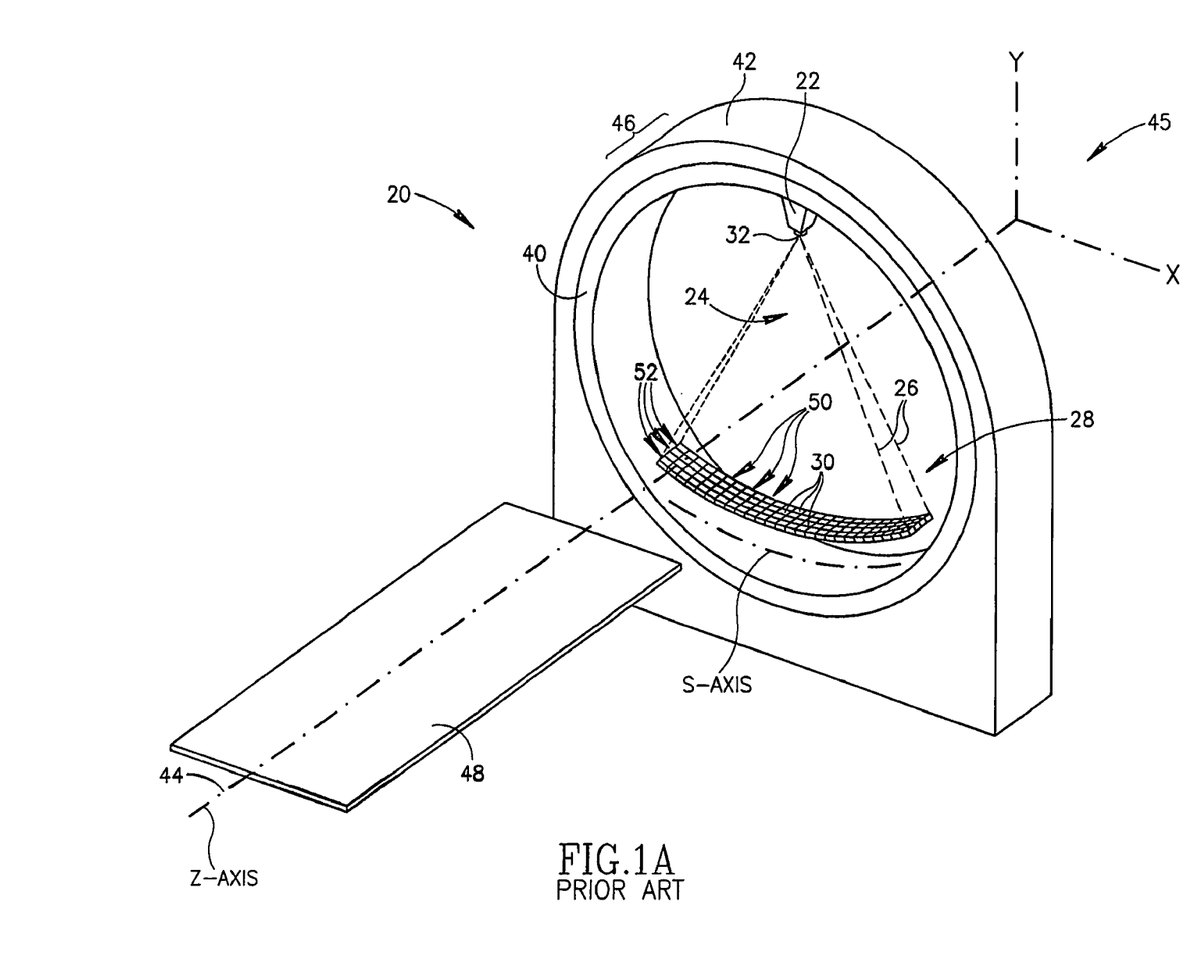
FIG. 1A schematically shows a third generation multislice CT scanner and its detector array, in accordance with prior art, but without AS foils that are used to shield X-ray detectors in the array.

FIG. 1A schematically shows a third generation multislice CT scanner 20, in accordance with prior art. Only those features and components of CT scanner 20 germane to the present discussion are shown in FIG. 1A.

CT scanner 20 comprises an X-ray source 22 controllable to provide an X-ray fan-beam 24, schematically indicated by dashed lines 26, and an array 28 of X-ray detectors 30. Fan-beam 24 emanates from a focal region 32, hereinafter referred to as "focal spot 32", of X-ray source 22. X-ray source 22 and detector array 28 are mounted to a rotor 40, which in turn is rotatably mounted to a stator 42 so that the rotor can be rotated about an axis 44 conveniently labeled as the z-axis of a coordinate system 45. Stator 42 and rotor 40 are components of a gantry 46 of CT scanner 20.

Figure 1B:
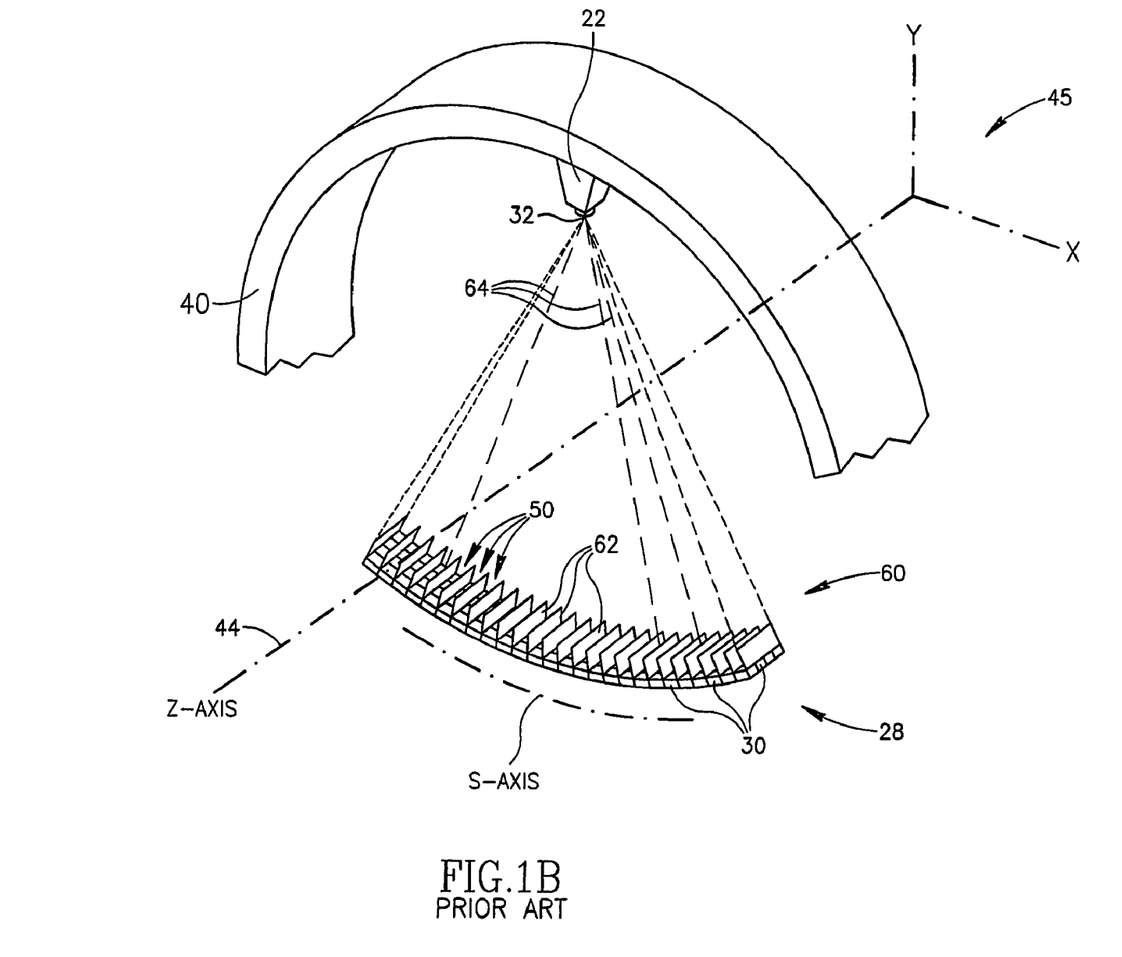
FIG. 1B schematically shows the X-ray detector array of the CT scanner shown in FIG. 1A and AS shielding used to shield X-ray detectors in the array, in accordance with prior art.

Array 28 has columns 50 and rows 52 of X-ray detectors 30. Array 28 is shown having four rows 52 of detectors to indicate, by way of example, that CT scanner 20 is a multislice scanner capable of imaging up to four slices of a patient at a time. Each row 52 of detectors is a curved row that lies substantially along an arc of a circle having its plane perpendicular to the z-axis and its center at focal spot 32 of X-ray source 22. A feature of X-ray detector array 28 is conveniently located by a z-coordinate determined with reference to the z-axis and an "s-coordinate" determined with reference to an s-axis shown alongside array 28. The s-axis is an arc of a circle having a same radius and center as the arc of the circle along which detectors in a row 52 of detectors are positioned. AS foils that are used to shield X-ray detectors 30 and reduce effects of scattered X-rays are not shown in FIG. 1A so as to display in FIG. 1A the configuration of X-ray detectors 30 in array 28. The AS foils are shown in FIG. 1B, discussed below.

It is noted that the number and relative size of X-ray detectors 30 shown in detector array 28 is arbitrary and chosen for convenience and clarity of presentation. In practice, an X-ray detector array in a typical multi slice CT scanner may comprise many thousands of small X-ray detectors having areas typically equal to about a square millimeter.

A patient to be imaged by CT scanner 20 is supported on a couch 48. Couch 48 is mounted on a suitable pedestal (not shown) and is controllable to be translated axially along z-axis 44 so as to position a region of the patient's body to be imaged by CT scanner 20 inside gantry 46, between X-ray source 22 and array 28. When the region to be imaged is properly positioned inside gantry 46, rotor 40 is controlled to rotate X-ray source 22 around the z-axis to illuminate the region with X-rays from a plurality of view angles. For each view angle, X-ray detectors 30 in array 28 generate signals responsive to intensity of X-rays from X-ray source 22 that pass through the region and that are incident on the detectors. The signals generated by X-ray detectors 30 in a same row 52 of detectors 30 are processed to generate an image of a slice of the region.

Ideally, each detector 30 measures intensity only of X-rays from X-ray source 22 that travel along a substantially straight-line path from the X-ray source through the region being imaged to the detector. To reduce errors in intensity measurements provided by detectors 30, which are generated by X-rays that do not reach the detectors along straight-line paths but reach the detectors after being scattered, AS foils are used to shield X-ray detectors 30 in array 28.

FIG. 1B schematically shows X-ray detector array 28 of CT scanner 20 shown in FIG. 1A and AS shielding 60 used to shield detectors 30 in the array in accordance with prior art. Also shown are a portion of rotor 40 of CT scanner 20 to which detector array 28 is mounted, and other features of CT scanner 20 germane to the discussion.

AS shielding 60 comprises an AS foil 62 placed between each column 50 (FIG. 1A) of detectors 30. Each AS foil 62, hereinafter referred to as a "z-foil", has its plane parallel to the z-axis and is oriented so that the plane intersects focal spot 32. To schematically illustrate the orientation of z-foils 62 relative to focal spot 32, for each of a few z-foils 62 a dashed line 64 coplanar with the z-foil extends from the z-foil to intersect focal spot 32. Typically, z-foils 62 are formed from Tungsten or Molybdenum foil having thickness in a range from about 0.05 millimeters to about 0.2 millimeters and extend from array 28 towards focal spot 32 to a height in a range from about 20 millimeters to about 40 millimeters.

As z-foils 62 are made higher, planarity, thickness and orientation of the foils must be controlled to finer tolerances in order to prevent undesirable shadowing of X-ray detectors 30 by the foils. Practically, for X-ray detectors having characteristic dimensions of about a millimeter, a maximum height to which z-foils 62 can be made is about 40 millimeters. As X-ray detectors become smaller, planarity, thickness and orientation of AS foils also have to be controlled to more stringent tolerances.

Figure 1C:
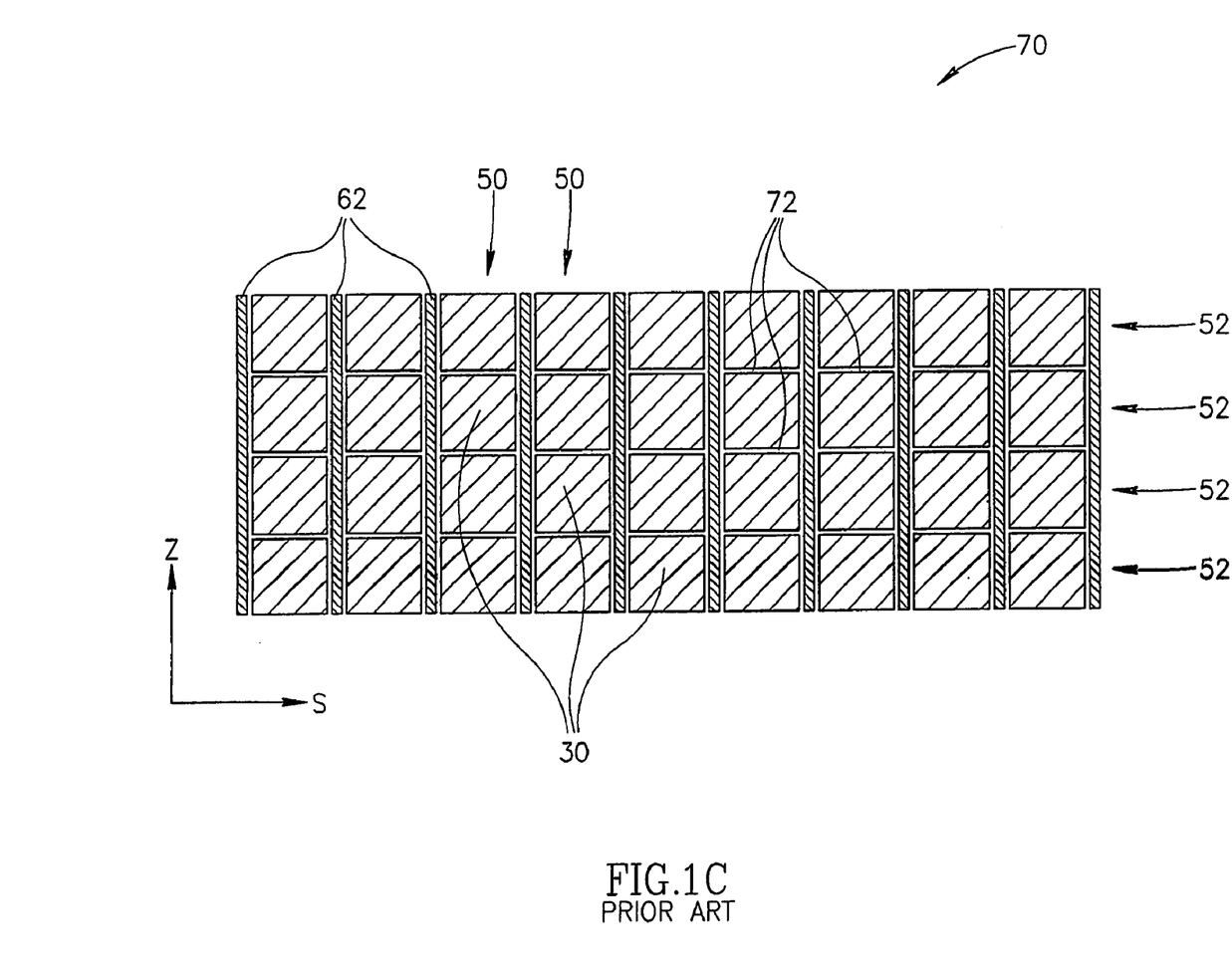
FIG. 1C schematically shows a plan view of the detector array and AS shielding shown in FIG. 1B, in accordance with prior art.

FIG. 1C shows a schematic plan view of a region 70 of detector array 28 shown in FIGS. 1A and 1B and z-foils 62, shown in FIG. 1B, associated with the region. For simplicity of presentation, region 70 of detector array 28 is shown in FIG. 1C as being planar. X-ray detectors 30 in detector array 28 that are comprised in region 70 are represented by lightly shaded squares and the z-axis and s-axis shown in FIGS. 1A and 1B are shown in FIG. 1C to orient region 70. Columns 50 of detectors 30 in region 70 are parallel to the z-axis and portions of rows 52 of detectors 30 that are comprised in the region are parallel to the s-axis.

A relatively narrow "isolation gap" 72 separates adjacent detectors 30 in a same column 50 of detectors 30. The width of isolation gaps 72 is usually made as small as possible in order to provide a packing density of X-ray detectors as large as possible. Typically, the width of isolation gaps 72 ranges from about 0.05 to about 0.3 millimeters.

Z-foils 62 are made as thin as possible consistent with effective shielding of X-ray detectors 30 to minimize space between columns 50 of the detectors. Motivation for minimizing thickness of z-foils 62 is to minimize the footprint of z-foils 62 on detector array 28 and provide for as large as possible a packing density of X-ray detectors 30 in array 28. As noted above, z-foils 62 are usually fabricated from Tungsten or Molybdenum and typically have a thickness in a range from about 0.05 to about 0.2 mm. As a result, adjacent columns 50 of detectors 30 are separated by a gap having a width generally in a range from about 0.2 to about 0.3 mm.

Figure 2:
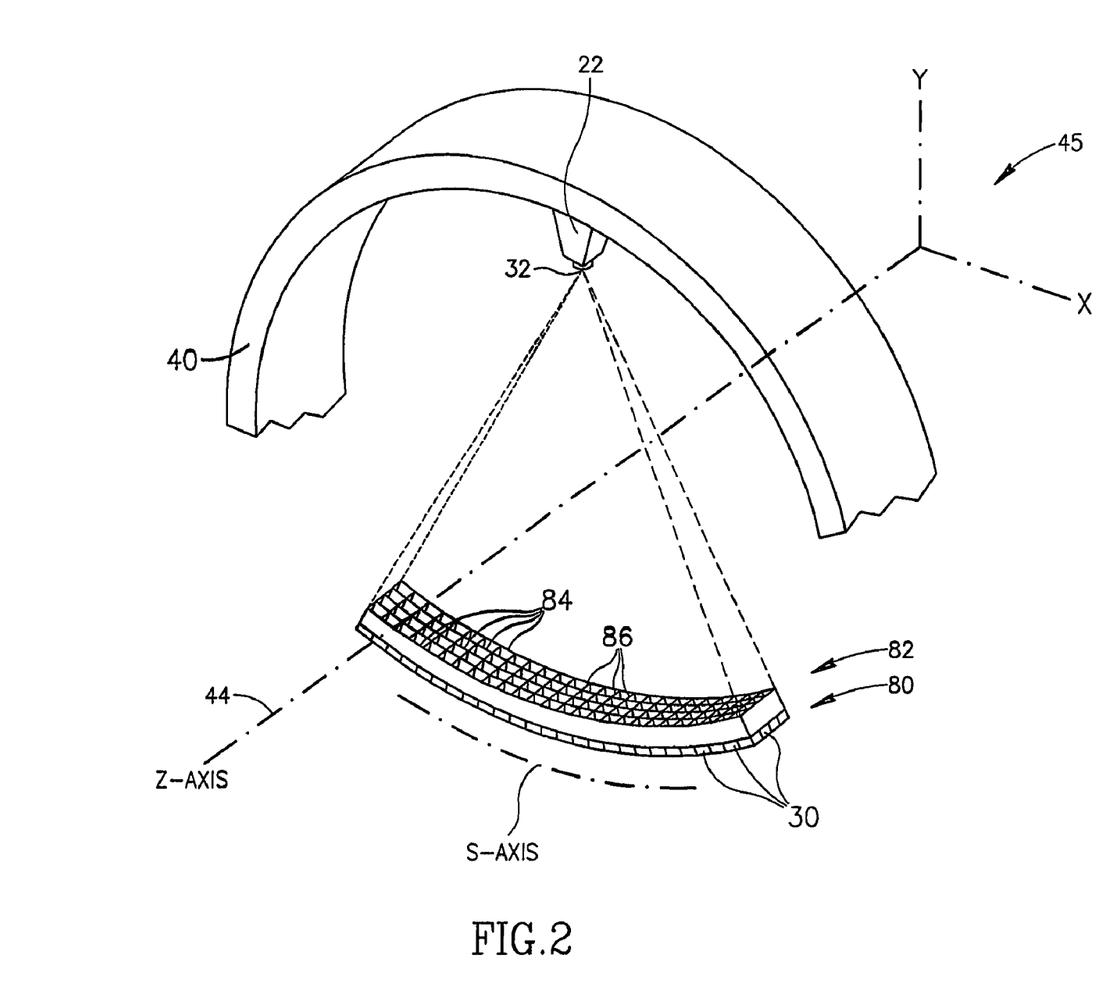
FIG. 2 schematically shows an X-ray detector array of a CT scanner having AS shielding, in accordance with an embodiment of the present invention.

FIG. 2 schematically shows an X-ray detector array 80 of a CT scanner (only parts of which are shown) and AS shielding 82 used to shield detectors 30 in the array, in accordance with an embodiment of the present invention. A portion of a rotor 40 of the CT scanner to which detector array 80 is mounted and the scanner's X-ray source 22 are also shown.

X-ray detector array 80 is similar to X-ray detector array 28 shown in FIG. 1A and FIG. 1B and detector array 80 is a two-dimensional array of columns 50 of X-ray detectors 30 parallel to the z-axis and rows 52 of X-ray detectors 30 parallel to the s-axis. Rows 52 and columns 50 of X-ray detectors 30 are not shown in the perspective of FIG. 2, but are shown in FIGS. 3A-3D discussed below, which show plan views of a region of detector array 28.

Whereas AS shielding 60 used with detector array 28 has AS foils, i.e. z-foils 62, (FIG. 1B and 1C) along a single direction, AS shielding 82, in accordance with an embodiment of the present invention, comprises AS foils aligned along at least two different directions. (As noted above, the direction of an AS foil is defined by the direction of the intersection line of the foil's plane with the surface of the detector array, as determined with reference to the z and s axes.) AS shielding 82 comprises AS foils 84, hereinafter referred to as "s-foils 84", parallel to the s-axis as well as z-foils 86, which are parallel to the z-axis. In accordance with an embodiment of the present invention, z and s-foils 86 and 84 are configured so that there is a z-foil 86 located between every other column 50 (FIGS. 3A-3D) of X-ray detectors 30 and an s-foil located between every other row 52 (FIGS. 3A-3D) of the X-ray detectors.

It is noted that whereas constructing an AS foil configuration having foils along two directions is generally more difficult than constructing an AS foil configuration in which the foils are along a same single direction, a "two-dimensional" foil configuration can be constructed using methods known in the art For example, a two-dimensional foil configuration comprising foils along two directions can be constructed by appropriately slotting the foils so that they can be inserted one into the slots of the other to form an array of "cubicles".

Figure 3A:
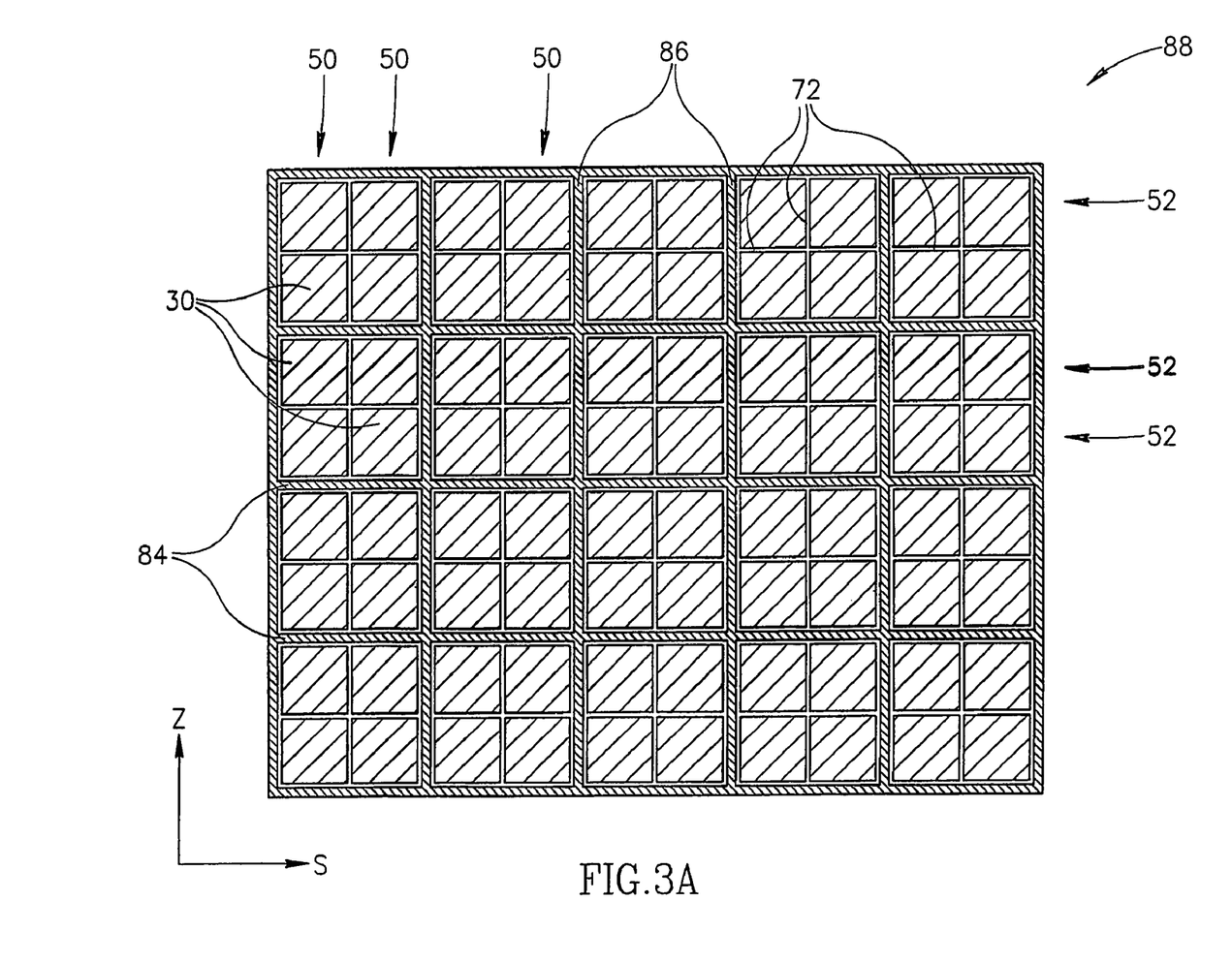
FIG. 3A schematically shows a plan view of the detector array and AS shielding shown in FIG. 2 and a configuration of z-axis and s-axis AS foils in the AS shielding, in accordance with an embodiment of the present invention.

FIG. 3A schematically shows a plan view of a region 88 of detector array 80. Columns 50 of detectors 30 are parallel to the z-axis shown at the right of region 88 and rows 52 of detectors 30 are parallel to the s-axis shown at the bottom of region 88. Whereas by way of example, detector array 80 is assumed to have at least eight rows 52 of detectors 30, it is noted that the present invention can be practiced with detector arrays having other than eight rows of detectors.

Shaded bands 84 represent s-foils, which are located between every other row 52 of detectors 30 and shaded bands 86 represent z-foils, which are located between every other column 50 of detectors 30. Isolation gaps 72 separate adjacent detectors 30 that are not separated by a z-foil 86 or an s-foil 84.

Optionally, z-foils 86 and s-foils 84 have a same thickness and are represented by shaded bands having a same width Optionally, z-foils 86 and s-foils 84 have a same height Z-foils 86 and s-foils 84 partition X-ray detectors 30 in detector array 80 into groups of four detectors. Each detector 30 in a group of detectors 30 has one edge adjacent to a z-foil 86 and one edge adjacent to an s-foil 84. Each of the other two edges of each detector 30 is adjacent to an isolation gap 72.

As a result of the configuration of z-foils 86 and s-foils 84, each X-ray detector 30 in array 28 is shielded by a substantially same configuration of AS foils. To within a rotation transformation, the configurations of AS foils 86 and 84 seen by any two detectors 30 in detector array 80 are substantially the same. Therefore, changes that AS shielding 82 might introduce into the intensity of direct or scattered X-rays reaching X-ray detectors 30, which could generate different effective detection efficiencies or "responsivities" for different X-ray detectors, are moderated.

AS shielding for a CT scanner detector array, in accordance with embodiments of the present invention, is optionally configured to provide an appropriate degree of symmetry so that the shielding does not generate substantial inhomogeneities in the spectra of X-rays reaching detectors in the array. Optionally, in AS shielding provided for a CT scanner, in accordance with an embodiment of the present invention, the configuration of AS foils comprised in the shielding that is seen by any two detectors in the CT scanner are substantially the same to within a rotation and/or parity transform.

Whereas, the configuration of z-foils 86 and s-foils 84 shown in FIG. 3A exhibits the optional degree of symmetry discussed in the preceding paragraph, the configuration shown in FIG. 3A is not the only configuration of AS foils, in accordance with embodiments of the present invention, that exhibits a desired degree of symmetry. AS shielding in accordance with embodiments of the present invention, having configurations of z-foils and s-foils different from that shown in FIG. 3A can be used to provide each detector 30 in detector array 80 with a substantially same configuration of AS foils.

Figure 3B:
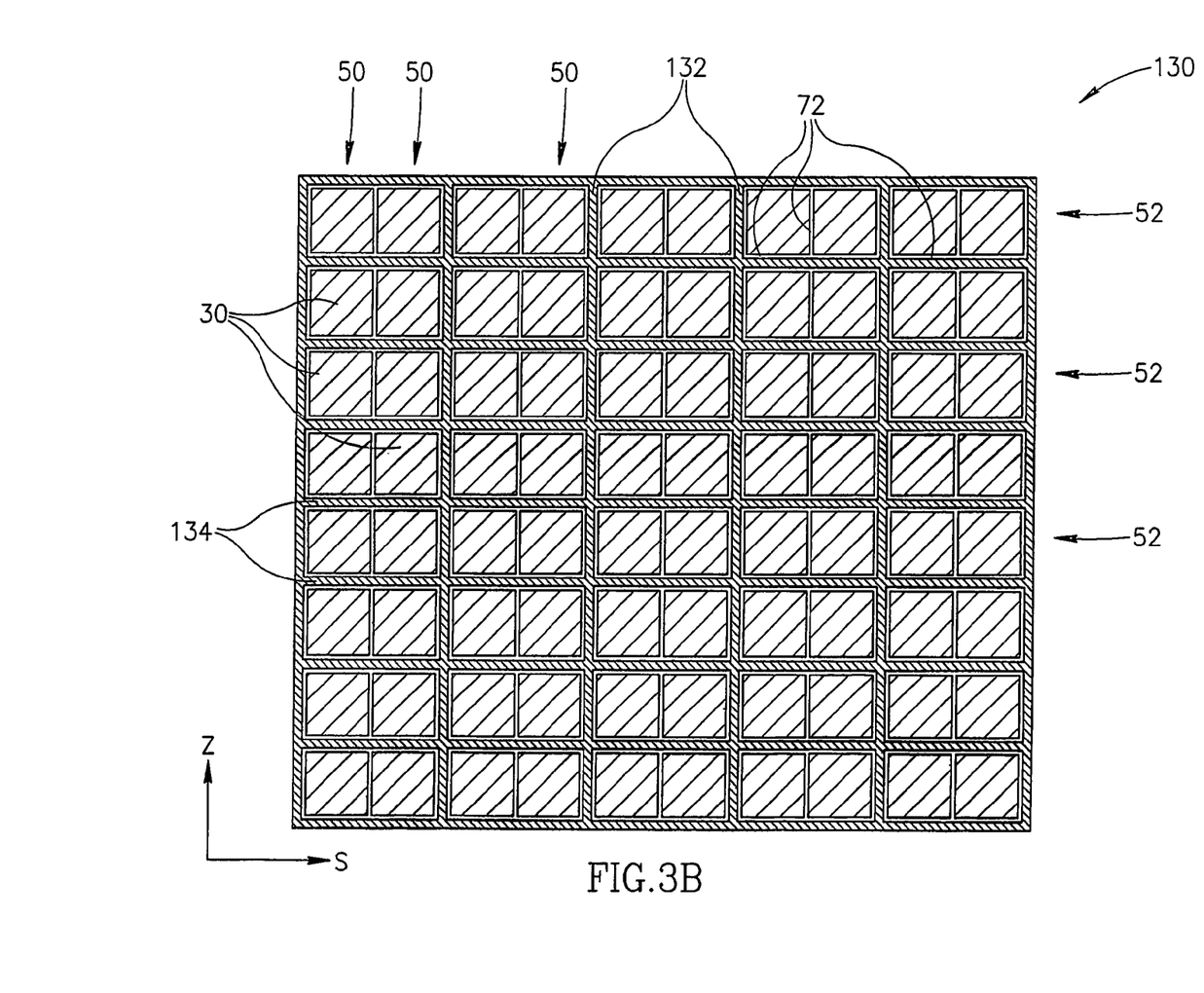
FIG. 3B schematically shows a plan view of an X-ray detector array and AS shielding having an alternative configuration of z-axis and s-axis, in accordance with an embodiment of the present invention.

For example, FIG. 3B schematically shows a plan view of a region 130 of a detector array similar to detector array 80 but having a configuration of z-foils 132 and s-foils 134, for which there is an s-foil between every row 52 of detectors 30 and between every other column 50 of the detectors. Detector arrays, in accordance with an embodiment of the present invention, for which there is an s-foil between every other row of detectors and a z-foil between every other column of detectors, is of course possible as well.

Figure 3C:
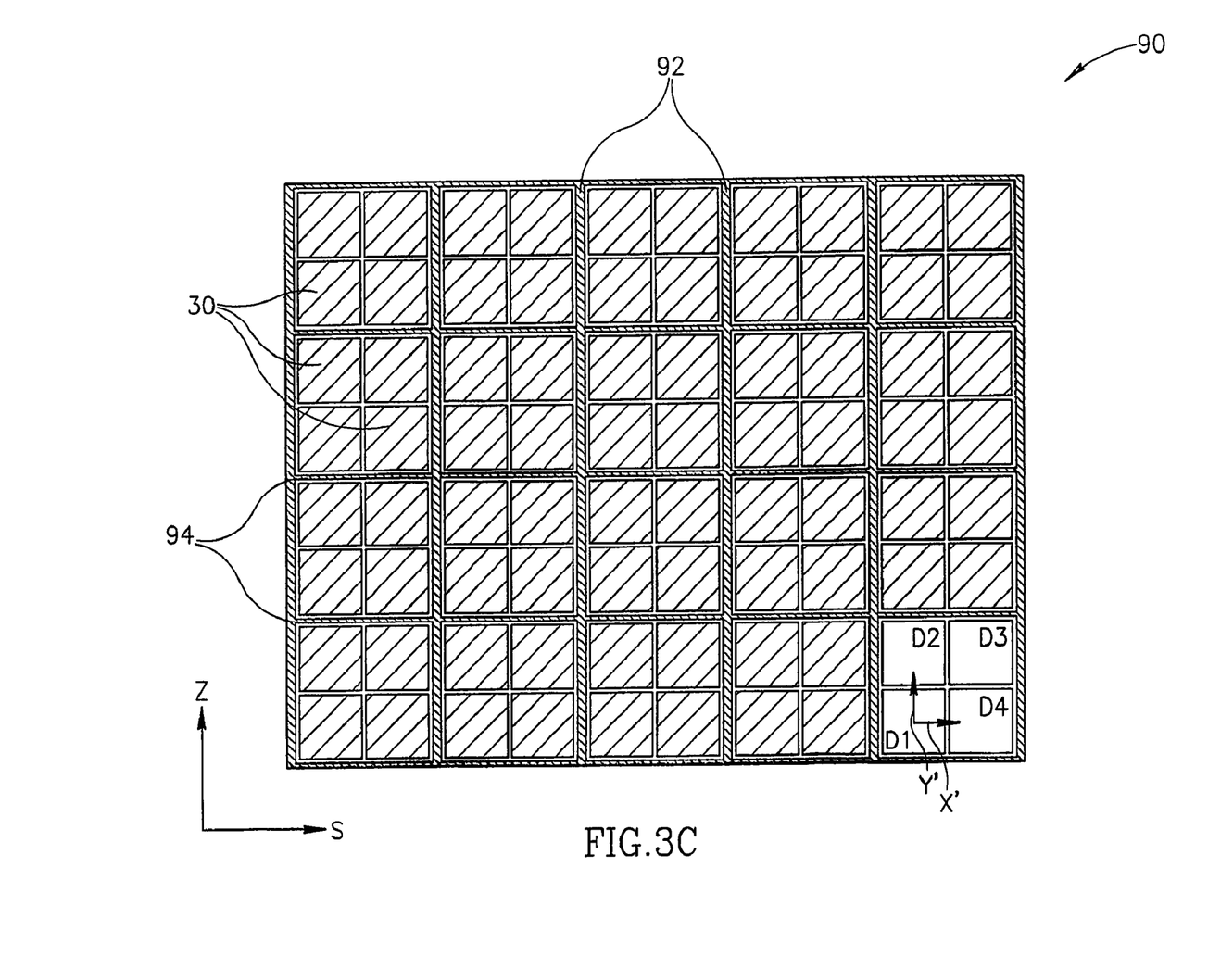
FIG. 3C schematically shows a plan view of an X-ray detector array and AS shielding having another alternative configuration of z-axis and s-axis, in accordance with an embodiment of the present invention.

By way of another example, FIG. 3C shows a plan view of a region 90 of a detector array similar to detector array 80 but having a configuration of z-foils 92 and s-foils 94, for which the thickness of s-foils 94 is different from the thickness of z-foils 92. By way of example, in FIG. 3C s-foils 94 are thinner than z-foils 92. For the AS foil configuration shown in FIG. 3C, to within a parity and rotation transformation the configuration of AS foils seen by any two detectors 30 in region 90 is identical.

To illustrate, detectors 30 in a group of four detectors along the lower right corner of region 90 are labeled D1-D4. Detector D1 is provided with a "local" coordinate system having x' and y' axis as shown and a z' axis (not shown) perpendicular to the plane of the figure and pointing towards the reader. Detector D1 has an AS shielding configuration in which a portion of a thin s-foil 94 is adjacent the detector's bottom edge and a portion of a thick z-foil 92 is adjacent the detector's left edge. D2 on the other hand has an AS shielding configuration for which a portion of a thin s-foil 94 is adjacent the detector's top edge and a portion of a thick z-foil 92 is adjacent the detector's left edge. If the portions of z-foil 92 and s-foil 94 adjacent the left and bottom edges of detector D1 are rotated by 180° about the z'-axis in the detector's local coordinate system, the z-foil and s-foil portions will end up respectively adjacent the top and right edges of detector D1. By switching the s-foil portion, which is after the 180° rotation located along the right edge of D1, to the left edge of D1, (i.e. a parity transform), D1 will have the same configuration of AS foils as detector D2. The shielding configuration of any detector D1-D4 can be transformed by a suitable rotation and/or parity transformation to the shielding configuration of any of the other detectors D1-D4.

Figure 3D:
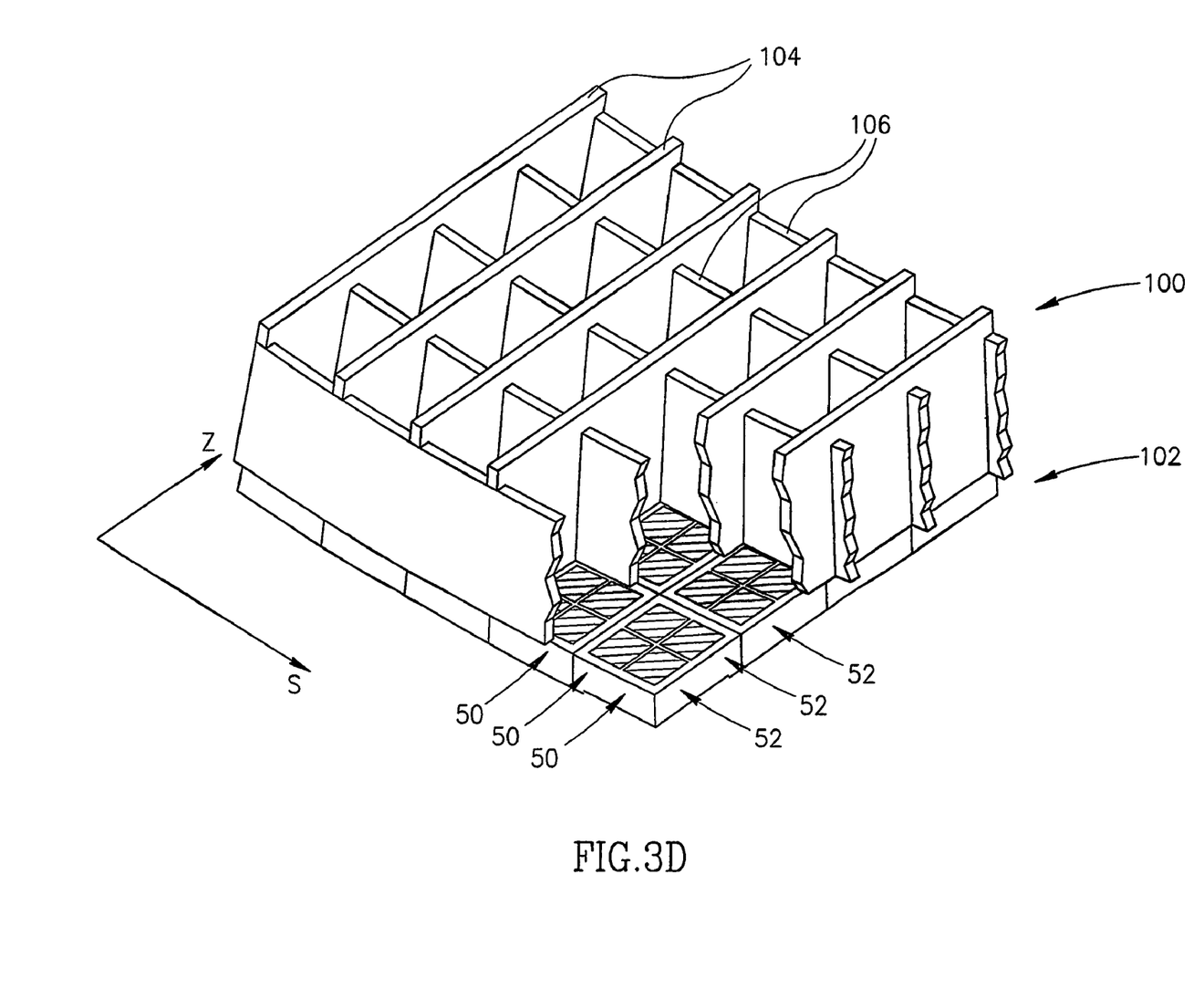
FIG. 3D schematically shows a partially cutaway perspective view of an X-ray detector array and AS shielding having a configuration of z-axis and s-axis AS foils in which z-axis and s-axis foils have different heights, in accordance with an embodiment of the present invention.

FIG. 3D shows a perspective partially cutaway view of AS shielding 100 for a region of a detector array 102 similar to detector array 80, in which z-axis and s-axis foils have different heights, in accordance with an embodiment of the present invention.

AS shielding 100 comprises z-foils 104 placed between every other column 50 of detectors 30 and s-foils 106 placed between every other row 52 of detectors 30. By way of example, the height of s-foils 106 is less than the height of z-foils 104. As in the case of the configuration of AS foils (z-foils 92 and s-foils 94) shown in FIG. 3C, for AS shielding 100 a configuration of z-foils 104 and s-foils 106 seen by any two detectors 30 is substantially the same to within a rotation and/or parity transform.

It is noted that in the examples of detector arrays and AS shielding shown in FIGS. 1A-3D, X-ray detectors in the detector arrays are square and have the same size. X-ray detectors in a CT scanner detector array may have shapes other than square, for example the detectors are often rectangular. Furthermore, a CT scanner detector array may comprise X-ray detectors having different shapes and or sizes. For example a detector array may comprise both square and rectangular X-ray detectors. Practice of the present invention is not limited to detector arrays comprising square detectors or detector arrays having detectors all of the same size and/or shape. The present invention may be practiced with CT scanner detector arrays comprising other than square detectors and detector arrays comprising detectors having different sizes and/or shapes. Symmetry considerations for configurations of AS shielding in accordance with embodiments of the present invention discussed above for detector arrays comprising square X-ray detectors apply equally well to detector arrays comprising non-square X-ray detectors and detector arrays comprising detectors of different size and/or shape.

Figure 3E:
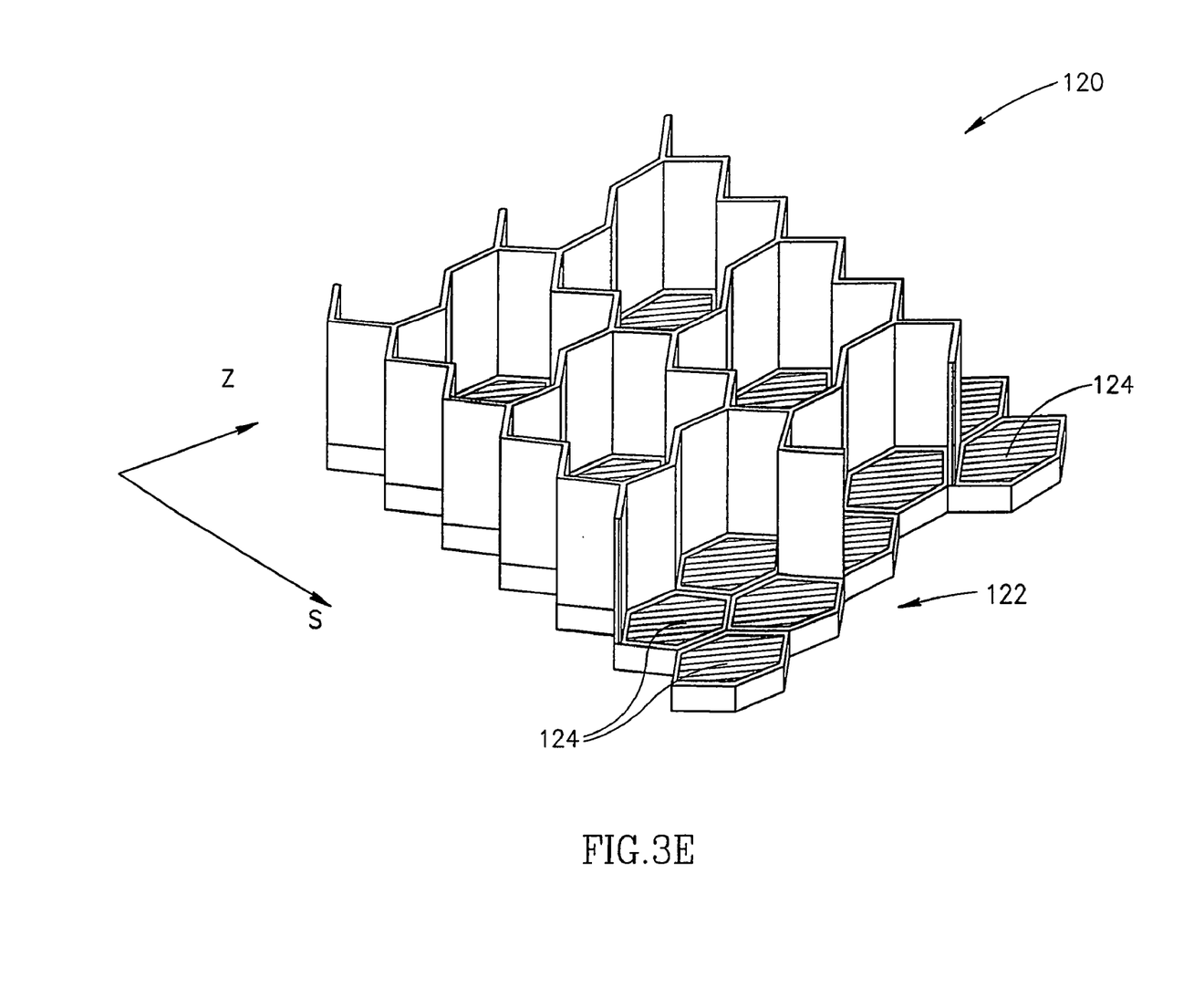
FIG. 3E schematically shows a partially cutaway perspective view of an X-ray detector array having hexagonal X-ray detectors and AS shielding therefore, in accordance with an embodiment of the present invention.

FIG. 3E schematically shows a configuration of AS shielding, 120 in accordance with an embodiment of the present invention, for an array 122 of detectors 124 in which detectors 124 are hexagonal. AS shielding, in accordance with an embodiment of the present invention, as seen by any detector 122, to within a rotation or parity transform is substantially the same for each detector.

It is also noted that whereas FIGS. 1A, 1B and 2 schematically show third generation CT scanners and detector arrays and/or parts thereof and FIGS. 3A-3D refer to detector arrays comprised in or similar to the detector arrays shown in FIGS. 1A, 1B and 2, the present invention is applicable to fourth generation as well as third generation CT scanners and X-ray detector arrays. FIGS. 3A-3D and discussions thereof, as noted above, are interpreted as referring to fourth generation detector arrays with rows or portions of rows of detectors referring to circles of detectors or portions of circles of detectors.

In the description and claims of the present application, each of the verbs, "comprise" "include" and "have", and conjugates thereof, are used to indicate that the object or objects of the verb are not necessarily a complete listing of members, components, elements or parts of the subject or subjects of the verb.

The present invention has been described using detailed descriptions of embodiments thereof that are provided by way of example and are not intended to limit the scope of the invention. The described embodiments comprise different features, not all of which are required in all embodiments of the invention. Some embodiments of the present invention utilize only some of the features or possible combinations of the features. Variations of embodiments of the present invention that are described and embodiments of the present invention comprising different combinations of feature noted in the described embodiments will occur to persons of the art. The scope of the invention is limited only by the following claims.

The invention claimed is:

1. A CT scanner comprising a stator and a rotor having an axis of rotation mounted to the stator so that the rotor is rotatable about the axis of rotation comprising:
    an X-ray source mounted to the rotor, said X-ray source having a focal spot from which X-rays emanate;
    an X-ray detector array comprising a matrix of rows and columns of X-ray detectors; anti-scattering (AS) material for absorbing X-rays positioned between columns of the X-ray detectors; and
    anti-scattering (AS) material for absorbing X-rays positioned between rows of the X-ray detectors; wherein as seen from a perspective of a first coordinate system located in substantially any first detector of the detector array and a homologous coordinate system located in substantially any second detector of the detector array, the AS material has substantially a same configuration to within a parity transformation and/or a rotation transformation; and wherein the AS material is located between every other row of detectors.

2. A CT scanner according to claim 1 wherein the AS material is formed in a shape of a thin foil for which for any point on the foil a segment of a line from the focal point of the X-ray source to the point lies substantially within or on the surface of the foil.

3. A CT scanner according to claim 2 wherein foil between columns of detectors extends towards the focal point to a height relative to the detector array that is different from a height to which foil located between rows of detectors extends towards the focal point.

4. A CT scanner according to claim 2 wherein thickness of the foil between rows is different from thickness of the foil between column.

5. A CT scanner according to claim 2 wherein the detectors have a hexagonal shape and the foil is shaped to follow the hexagonal shape of the detectors.

6. A CT scanner comprising a stator and a rotor having an axis of rotation mounted to the stator so that the rotor is rotatable about the axis of rotation comprising:
    an X-ray source mounted to the rotor, said X-ray source having a focal spot from which X-rays emanate;

an X-ray detector array comprising a matrix of rows and columns of X-ray detectors; anti-scattering (AS) material for absorbing X-rays positioned between columns of the X-ray detectors; and anti-scattering (AS) material for absorbing X-rays positioned between rows of the X-ray detectors; wherein as seen from a perspective of a first coordinate system located in substantially any first detector of the detector array and a homologous coordinate system located in substantially any second detector of the detector array, the AS material has substantially a same configuration to within a parity transformation and/or a rotation transformation; and wherein the AS material is located between every other column of detectors.

7. A CT scanner according to claim 6 wherein the AS material is formed in a shape of a thin foil for which for any point on the foil a segment of a line from the focal point of the X-ray source to the point lies substantially within or on the surface of the foil.

8. A CT scanner according to claim 7 wherein foil between columns of detectors extends towards the focal point to a height relative to the detector array that is different from a height to which foil located between rows of detectors extends towards the focal point.

9. A CT scanner according to claim 7 wherein thickness of the foil between rows is different from thickness of the foil between column.

10. A CT scanner according to claim 7 wherein the detectors have a hexagonal shape and the foil is shaped to follow the hexagonal shape of the detectors.

* * * * *